(12) United States Patent
Wu et al.

(10) Patent No.: US 7,256,268 B1
(45) Date of Patent: Aug. 14, 2007

(54) HUMAN HIGH AFFINITY CHOLINE TRANSPORTER

(75) Inventors: Dong-Hai Wu, Gainesville, FL (US); Yunrong Gu, Gainesville, FL (US); William James Millard, Gainesville, FL (US); Yun-Ju He, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 11/586,208

(22) Filed: Oct. 24, 2006

Related U.S. Application Data

(62) Division of application No. 10/271,090, filed on Oct. 15, 2002, which is a division of application No. 09/657,252, filed on Sep. 7, 2000, now Pat. No. 6,500,643.

(51) Int. Cl.
  C07H 21/04    (2006.01)
  G01N 33/567   (2006.01)
  C12P 21/06    (2006.01)
  C12N 1/20     (2006.01)
  C12N 15/00    (2006.01)
  C07K 14/00    (2006.01)
  C07K 9/00     (2006.01)

(52) U.S. Cl. ............... 530/350; 530/300; 530/329; 536/23.5; 435/7.21; 435/69.1; 435/252.3; 435/320.1; 436/501

(58) Field of Classification Search .................. None
See application file for complete search history.

(56) References Cited

U.S. PATENT DOCUMENTS 5,756,102 A    5/1998   Paolettie et al.

OTHER PUBLICATIONS

Accession No. AB030947, published Feb. 3, 2000.
GenBank Accession No. CAC03717 published Aug. 16, 2000.
Alexander, et al., "Altering the antigenicity of proteins", Proc. Natl. Acad. Sci. 89(3352-3356) 1992.
Guo-HH et al., "Protein tolerance to random amino acid change", PNAS 101(25)9205-9210, 2004.
Bowie et al., "Deciphering the message in protein sequences: tolerance to amino acid substitutions", Science 247:1306-1310, 1990.
Happe & Martin, "High Affinity Choline Transport Sites' Use of [$^3$H]Hemicholinium-3 as a Quantitative Marker", Neurochem, 60:1191-1201 (1993); Raven Press, Ltd. New York.
Rylett et al., "Affinity Labelling and Identification of the High-Affinity Choline Carrier from Synaptic Membranes of Torpedo Electromotor Nerve Terminals with [$^3$H]Choline Mustard". J. Neurochem 51:1942-5 (1988).
Knipper et al., "Isolation and Reconstitution of the High-Affinity Choline Carrier", FEBS Lett. 245:235-237 (1989).
Knipper et al., "Hemicholinum-3 Biding Sites in the Nervous Tissue of Insects" Neurochem, Int. 14:211-215 (1989).
Knipper et al., "Purification and Reconstitution of the High Affinity Choline Transporter", Biochem. Biophys. Acta, 1065:107-113 (1991).
O'Regan et al., Regulation of Hemicholinium-3 Sensitive Choline Uptake in *Xenopus laevis* Oocytes by the Second C2 Domain of Synaptotagmin., Mol. Brain Res. 32:135-42 (1994).
Mayser et al., "Primary Structure and Functional Expression of a Choline Transporter Expressed in the Rat Nervous System," FEBS Lett. 305:31-36 (1992).
Apparsundaram et al., Molecular Cloning of a Human, Hemicholinium-3-Sensitive Choline Transporter, Biochem. Biophys. Res. Comm. 276:862-867 (2000).
Okuda et al., "Identification and characterization of the High-Affinity Choline Transporter", Natl. Neurosci. 31:120-5 (2000).
Kanai & Hediger, Primary Structure and Functional Characterization of a high-affinity Glutamate Transporter, Nature, 360:467 (1992).
NCBI Accession No. AB030947, Okuda, et al., Feb. 3, 2000, National Center for Biotechnology Information, Bethesda, MD.
NCBI Accession No. AB030946, Okuda, et al., Feb. 3, 2000, National Center for Biotechnology Information, Bethesda, MD.
NCBI Accession No. BB422667; Hayashizaki, Jul. 16, 2000, National Center for Biotechnology Information, Bethesda, MD.
NCBI Accession No. BB192558; Hayashizaki, Jun. 30, 2000, National Center for Biotechnology Information, Bethesda, MD.
NCBI Accession No. AF276871; Apparsundaram, et al., Oct. 25, 2000, National Center for Biotechnology Information, Bethesda, MD.
NCBI Accession No. AJ401467; Weiland et al., Aug. 16, 2000; National Center for Biotechnology Information, Bethesda, MD.
NCBI Accession No. AJ401466; Weiland et al., Aug. 16, 2000; National Center for Biotechnology Information, Bethesda, MD.

*Primary Examiner*—Janet L. Andres
*Assistant Examiner*—Michael Brannock
(74) *Attorney, Agent, or Firm*—McDonnell Boehnen Hulbert & Berghoff LLP

(57) ABSTRACT

The invention provides human high affinity choline transporter polynucleotides and polypeptides and compositions comprising human high affinity choline transporter polynucleotides and polypeptides.

2 Claims, 2 Drawing Sheets
(1 of 2 Drawing Sheet(s) Filed in Color)

SEQUENCE LISTING

<160> NUMBER OF SEQ ID NOS: 6

<210> SEQ ID NO 1
<211> LENGTH: 1743
<212> TYPE: DNA
<213> ORGANISM: Homo sapiens
<220> FEATURE:
<221> NAME/KEY: CDS
<222> LOCATION: (1)..(1743)

<400> SEQUENCE: 1

```
atg gct ttc cat gtg gaa gga ctg ata gct atc atc gtg ttc tac ctt        48
Met Ala Phe His Val Glu Gly Leu Ile Ala Ile Ile Val Phe Tyr Leu
1               5                   10                  15 cta att ttg ctg gtt gga ata tgg gct gcc tgg aga acc aaa aac agt        96
Leu Ile Leu Leu Val Gly Ile Trp Ala Ala Trp Arg Thr Lys Asn Ser
            20                  25                  30 ggc agc gca gaa gag cgc agc gaa gcc atc ata gtt ggt ggc cga gat       144
Gly Ser Ala Glu Glu Arg Ser Glu Ala Ile Ile Val Gly Gly Arg Asp
        35                  40                  45 att ggt tta ttg gtt ggt gga ttt acc atg aca gct acc tgg gtc gga       192
Ile Gly Leu Leu Val Gly Gly Phe Thr Met Thr Ala Thr Trp Val Gly
    50                  55                  60 gga ggg tat atc aat ggc aca gct gaa gca gtt tat gta cca ggt tat       240
Gly Gly Tyr Ile Asn Gly Thr Ala Glu Ala Val Tyr Val Pro Gly Tyr
65                  70                  75                  80 ggc cta gct tgg gct cag gca cca att gga tat tct ctt agt ctg att       288
Gly Leu Ala Trp Ala Gln Ala Pro Ile Gly Tyr Ser Leu Ser Leu Ile
                85                  90                  95 tta ggt ggc ctg ttc ttt gca aaa cct atg cgt tca aag ggg tat gtg       336
Leu Gly Gly Leu Phe Phe Ala Lys Pro Met Arg Ser Lys Gly Tyr Val
            100                 105                 110 acc atg tta gac ccg ttt cag caa atc tat gga aaa cgc atg ggc gga       384
Thr Met Leu Asp Pro Phe Gln Gln Ile Tyr Gly Lys Arg Met Gly Gly
        115                 120                 125 ctc ctg ttt att cct gca ctg atg gga gaa atg ttc tgg gct gca gca       432
Leu Leu Phe Ile Pro Ala Leu Met Gly Glu Met Phe Trp Ala Ala Ala
    130                 135                 140 att ttc tct gct ttg gga gcc acc atc agc gtg atc atc gat gtg gat       480
Ile Phe Ser Ala Leu Gly Ala Thr Ile Ser Val Ile Ile Asp Val Asp
145                 150                 155                 160 atg cac att tct gtc atc atc tct gca ctc att gcc act ctg tac aca       528
Met His Ile Ser Val Ile Ile Ser Ala Leu Ile Ala Thr Leu Tyr Thr
                165                 170                 175 ctg gtg gga ggg ctc tat tct gtg gcc tac act gat gtc gtt cag ctc       576
Leu Val Gly Gly Leu Tyr Ser Val Ala Tyr Thr Asp Val Val Gln Leu
            180                 185                 190
```

-continued

| | |
|---|---|
| ttt tgc att ttt gta ggg ctg tgg atc agc gtc ccc ttt gca ttg tca<br>Phe Cys Ile Phe Val Gly Leu Trp Ile Ser Val Pro Phe Ala Leu Ser<br>195                                        200                                205 | 624 |
| cat cct gca gtc gca gac atc ggg ttc act gct gtg cat gcc aaa tac<br>His Pro Ala Val Ala Asp Ile Gly Phe Thr Ala Val His Ala Lys Tyr<br>    210                                215                                220 | 672 |
| caa aag ccg tgg ctg gga act gtt gac tca tct gaa gtc tac tct tgg<br>Gln Lys Pro Trp Leu Gly Thr Val Asp Ser Ser Glu Val Tyr Ser Trp<br>225                                      230                            235                      240 | 720 |
| ctt gat agt ttt ctg ttg ttg atg ctg ggt gga atc cca tgg caa gca<br>Leu Asp Ser Phe Leu Leu Leu Met Leu Gly Gly Ile Pro Trp Gln Ala<br>                          245                                250                            255 | 768 |
| tac ttt cag agg gtt ctc tct tct tca gcc acc tat gct caa gtg<br>Tyr Phe Gln Arg Val Leu Ser Ser Ser Ala Thr Tyr Ala Gln Val<br>          260                            265                            270 | 816 |
| ctg tcc ttc ctg gca gct ttc ggg tgc ctg gtg atg gcc atc cca gcc<br>Leu Ser Phe Leu Ala Ala Phe Gly Cys Leu Val Met Ala Ile Pro Ala<br>275                                      280                            285 | 864 |
| ata ctc att ggg gcc att gga gcc tcc aca gac tgg aac cag act gca<br>Ile Leu Ile Gly Ala Ile Gly Ala Ser Thr Asp Trp Asn Gln Thr Ala<br>    290                                295                                300 | 912 |
| tat ggg ctt cca gat ccc aag act aca gaa gag gca gac atg att tta<br>Tyr Gly Leu Pro Asp Pro Lys Thr Thr Glu Glu Ala Asp Met Ile Leu<br>305                                      310                            315                      320 | 960 |
| cca att gtt ctg cag tat ctc tgc cct gtg tat att tct ttc ttt ggt<br>Pro Ile Val Leu Gln Tyr Leu Cys Pro Val Tyr Ile Ser Phe Phe Gly<br>                          325                                330                            335 | 1008 |
| ctt ggt gca gtt tct gct gct gtt atg tca tca gca gat tct tcc atc<br>Leu Gly Ala Val Ser Ala Ala Val Met Ser Ser Ala Asp Ser Ser Ile<br>                    340                              345                            350 | 1056 |
| ttg tca gca agt tcc atg ttt gca cgg aac atc tac cag ctt tcc ttc<br>Leu Ser Ala Ser Ser Met Phe Ala Arg Asn Ile Tyr Gln Leu Ser Phe<br>355                                      360                            365 | 1104 |
| aga caa aat gct tcg gac aaa gaa atc gtt tgg gtt atg cga atc aca<br>Arg Gln Asn Ala Ser Asp Lys Glu Ile Val Trp Val Met Arg Ile Thr<br>    370                                375                              380 | 1152 |
| gtg ttt gtg ttt gga gca tct gca aca gcc atg gcc ttg ctg acg aaa<br>Val Phe Val Phe Gly Ala Ser Ala Thr Ala Met Ala Leu Leu Thr Lys<br>385                                      390                            395                      400 | 1200 |
| act gtg tat ggg ctc tgg tac ctc agt tct gac ctt gtt tac atc gtt<br>Thr Val Tyr Gly Leu Trp Tyr Leu Ser Ser Asp Leu Val Tyr Ile Val<br>                    405                              410                            415 | 1248 |
| atc ttc ccc cag ctg ctt tgt gta ctc ttt gtt aag gga acc aac acc<br>Ile Phe Pro Gln Leu Leu Cys Val Leu Phe Val Lys Gly Thr Asn Thr<br>                    420                              425                            430 | 1296 |
| tat ggg gcc gtg gca ggt tat gtt tct ggc ctc ttc ctg aga ata act<br>Tyr Gly Ala Val Ala Gly Tyr Val Ser Gly Leu Phe Leu Arg Ile Thr<br>435                                      440                            445 | 1344 |
| gga ggg gag cca tat ctg tat ctt cag ccc ttg atc ttc tac cct ggc<br>Gly Gly Glu Pro Tyr Leu Tyr Leu Gln Pro Leu Ile Phe Tyr Pro Gly<br>    450                                455                              460 | 1392 |
| tat tac cct gat gat aat ggt ata tat aat cag aaa ttt cca ttt aaa<br>Tyr Tyr Pro Asp Asp Asn Gly Ile Tyr Asn Gln Lys Phe Pro Phe Lys<br>465                                      470                            475                      480 | 1440 |
| aca ctt gcc atg gtt aca tca ttc tta acc aac att tgc atc tcc tat<br>Thr Leu Ala Met Val Thr Ser Phe Leu Thr Asn Ile Cys Ile Ser Tyr<br>                    485                              490                            495 | 1488 |
| cta gcc aag tat cta ttt gaa agt gga acc ttg cca cct aaa tta gat<br>Leu Ala Lys Tyr Leu Phe Glu Ser Gly Thr Leu Pro Pro Lys Leu Asp<br>                  500                              505                            510 | 1536 |

-continued

```
gta ttt gat gct gtt gtt gca aga cac agt gaa gaa aac atg gat aag    1584
Val Phe Asp Ala Val Val Ala Arg His Ser Glu Glu Asn Met Asp Lys
    515                 520                 525 aca att ctt gtc aaa aat gaa aat att aaa tta gat gaa ctt gca ctt    1632
Thr Ile Leu Val Lys Asn Glu Asn Ile Lys Leu Asp Glu Leu Ala Leu
530                 535                 540 gtg aag cca cga cag agc atg acc ctc agc tca act ttc acc aat aaa    1680
Val Lys Pro Arg Gln Ser Met Thr Leu Ser Ser Thr Phe Thr Asn Lys
545                 550                 555                 560 gag gcc ttc ctt gat gtt gat tcc agt cca gaa ggg tct ggg act gaa    1728
Glu Ala Phe Leu Asp Val Asp Ser Ser Pro Glu Gly Ser Gly Thr Glu
                565                 570                 575 gat aat tta caa tga                                                 1743
Asp Asn Leu Gln
            580

<210> SEQ ID NO 2
<211> LENGTH: 580
<212> TYPE: PRT
<213> ORGANISM: Homo sapiens

<400> SEQUENCE: 2

Met Ala Phe His Val Glu Gly Leu Ile Ala Ile Ile Val Phe Tyr Leu
1               5                   10                  15

Leu Ile Leu Leu Val Gly Ile Trp Ala Ala Trp Arg Thr Lys Asn Ser
                20                  25                  30

Gly Ser Ala Glu Glu Arg Ser Glu Ala Ile Ile Val Gly Gly Arg Asp
            35                  40                  45

Ile Gly Leu Leu Val Gly Gly Phe Thr Met Thr Ala Thr Trp Val Gly
        50                  55                  60

Gly Gly Tyr Ile Asn Gly Thr Ala Glu Ala Val Tyr Val Pro Gly Tyr
65                  70                  75                  80

Gly Leu Ala Trp Ala Gln Ala Pro Ile Gly Tyr Ser Leu Ser Leu Ile
                85                  90                  95

Leu Gly Gly Leu Phe Phe Ala Lys Pro Met Arg Ser Lys Gly Tyr Val
            100                 105                 110

Thr Met Leu Asp Pro Phe Gln Gln Ile Tyr Gly Lys Arg Met Gly Gly
        115                 120                 125

Leu Leu Phe Ile Pro Ala Leu Met Gly Glu Met Phe Trp Ala Ala Ala
130                 135                 140

Ile Phe Ser Ala Leu Gly Ala Thr Ile Ser Val Ile Ile Asp Val Asp
145                 150                 155                 160

Met His Ile Ser Val Ile Ile Ser Ala Leu Ile Ala Thr Leu Tyr Thr
                165                 170                 175

Leu Val Gly Gly Leu Tyr Ser Val Ala Tyr Thr Asp Val Val Gln Leu
            180                 185                 190

Phe Cys Ile Phe Val Gly Leu Trp Ile Ser Val Pro Phe Ala Leu Ser
        195                 200                 205

His Pro Ala Val Ala Asp Ile Gly Phe Thr Ala Val His Ala Lys Tyr
    210                 215                 220

Gln Lys Pro Trp Leu Gly Thr Val Asp Ser Ser Glu Val Tyr Ser Trp
225                 230                 235                 240

Leu Asp Ser Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
            260                 265                 270
```

```
Leu Ser Phe Leu Ala Ala Phe Gly Cys Leu Val Met Ala Ile Pro Ala
            275                 280                 285

Ile Leu Ile Gly Ala Ile Gly Ala Ser Thr Asp Trp Asn Gln Thr Ala
        290                 295                 300

Tyr Gly Leu Pro Asp Pro Lys Thr Thr Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
            340                 345                 350

Leu Ser Ala Ser Ser Met Phe Ala Arg Asn Ile Tyr Gln Leu Ser Phe
        355                 360                 365

Arg Gln Asn Ala Ser Asp Lys Glu Ile Val Trp Val Met Arg Ile Thr
    370                 375                 380

Val Phe Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Val
                405                 410                 415

Ile Phe Pro Gln Leu Leu Cys Val Leu Phe Val Lys Gly Thr Asn Thr
            420                 425                 430

Tyr Gly Ala Val Ala Gly Tyr Val Ser Gly Leu Phe Leu Arg Ile Thr
        435                 440                 445

Gly Gly Glu Pro Tyr Leu Tyr Leu Gln Pro Leu Ile Phe Tyr Pro Gly
    450                 455                 460

Tyr Tyr Pro Asp Asp Asn Gly Ile Tyr Asn Gln Lys Phe Pro Phe Lys
465                 470                 475                 480

Thr Leu Ala Met Val Thr Ser Phe Leu Thr Asn Ile Cys Ile Ser Tyr
                485                 490                 495

Leu Ala Lys Tyr Leu Phe Glu Ser Gly Thr Leu Pro Pro Lys Leu Asp
            500                 505                 510

Val Phe Asp Ala Val Val Ala Arg His Ser Glu Glu Asn Met Asp Lys
        515                 520                 525

Thr Ile Leu Val Lys Asn Glu Asn Ile Lys Leu Asp Glu Leu Ala Leu
    530                 535                 540

Val Lys Pro Arg Gln Ser Met Thr Leu Ser Ser Thr Phe Thr Asn Lys
545                 550                 555                 560

Glu Ala Phe Leu Asp Val Asp Ser Ser Pro Glu Gly Ser Gly Thr Glu
                565                 570                 575

Asp Asn Leu Gln
            580

<210> SEQ ID NO 3
<211> LENGTH: 1893
<212> TYPE: DNA
<213> ORGANISM: Homo sapiens
<220> FEATURE:
<221> NAME/KEY: CDS
<222> LOCATION: (1)..(1893)

<400> SEQUENCE: 3 atg gca gca aaa act ccc agc agt gag gag tct ggg ctg ccc aaa ctg      48
Met Ala Ala Lys Thr Pro Ser Ser Glu Glu Ser Gly Leu Pro Lys Leu
1               5                   10                  15 ccc gtg ccc ccg ctg cag cag acc ctg gcc acg tac ctg cag tgc atg      96
Pro Val Pro Pro Leu Gln Gln Thr Leu Ala Thr Tyr Leu Gln Cys Met
            20                  25                  30
```

-continued

| | |
|---|---|
| cga cac ttg gtg tct gag gag cag ttc agg aag agc cag gcc att gtg<br>Arg His Leu Val Ser Glu Glu Gln Phe Arg Lys Ser Gln Ala Ile Val<br>     35                    40                  45 | 144 |
| cag cag ttt ggg gcc cct ggt ggc ctc ggc gag acc ctg cag cag aaa<br>Gln Gln Phe Gly Ala Pro Gly Gly Leu Gly Glu Thr Leu Gln Gln Lys<br>50                   55                   60 | 192 |
| ctc ctg gag cgg cag gag aag aca gcc aac tgg gtg tct gag tac tgg<br>Leu Leu Glu Arg Gln Glu Lys Thr Ala Asn Trp Val Ser Glu Tyr Trp<br>65                  70                   75                  80 | 240 |
| ctg aat gac atg tat ctc aac aac cgc ctg gcc ctg cct gtc aac tcc<br>Leu Asn Asp Met Tyr Leu Asn Asn Arg Leu Ala Leu Pro Val Asn Ser<br>                 85                   90                   95 | 288 |
| agc cct gcc gtg atc ttt gct cgg cag cac ttc cct ggc acc gat gac<br>Ser Pro Ala Val Ile Phe Ala Arg Gln His Phe Pro Gly Thr Asp Asp<br>            100                   105               110 | 336 |
| cag ctg agg ttt gca gcc agc ctc atc tct ggt gta ctc agc tac aag<br>Gln Leu Arg Phe Ala Ala Ser Leu Ile Ser Gly Val Leu Ser Tyr Lys<br>            115                   120               125 | 384 |
| gcc ctg ctg gac agc cac tcc att ccc act gac tgt gcc aaa ggc cag<br>Ala Leu Leu Asp Ser His Ser Ile Pro Thr Asp Cys Ala Lys Gly Gln<br>130                     135               140 | 432 |
| ctg tca ggg cag ccc ctt tgc atg aag caa tac tat ggg ctc ttc tcc<br>Leu Ser Gly Gln Pro Leu Cys Met Lys Gln Tyr Tyr Gly Leu Phe Ser<br>145                     150               155               160 | 480 |
| tcc tac cgg ctc ccc ggc cat acc cag gac acg ttg gtg gct cag aac<br>Ser Tyr Arg Leu Pro Gly His Thr Gln Asp Thr Leu Val Ala Gln Asn<br>                 165                   170               175 | 528 |
| agc agc atc atg ccg gag cct gag cac gtc atc gta gcc tgc tgc aat<br>Ser Ser Ile Met Pro Glu Pro Glu His Val Ile Val Ala Cys Cys Asn<br>            180                   185               190 | 576 |
| cag ttc ttt gtc ttg gat gtt gtc att aat ttc cgc cgt ctc agt gag<br>Gln Phe Phe Val Leu Asp Val Val Ile Asn Phe Arg Arg Leu Ser Glu<br>            195                   200               205 | 624 |
| ggg gat ctg ttc act cag ttg aga aag ata gtc aaa atg gct tcc aac<br>Gly Asp Leu Phe Thr Gln Leu Arg Lys Ile Val Lys Met Ala Ser Asn<br>210                     215               220 | 672 |
| gag gac gag cgt ttg cct cca att ggc ctg ctg acg tct gac ggg agg<br>Glu Asp Glu Arg Leu Pro Pro Ile Gly Leu Leu Thr Ser Asp Gly Arg<br>225                     230               235               240 | 720 |
| agc gag tgg gcc gag gcc agg acg gtc ctc gtg aaa gac tcc acc aac<br>Ser Glu Trp Ala Glu Ala Arg Thr Val Leu Val Lys Asp Ser Thr Asn<br>                 245                   250               255 | 768 |
| cgg gac tcg ctg gac atg att gag cgc tgc atc tgc ctt gta tgc ctg<br>Arg Asp Ser Leu Asp Met Ile Glu Arg Cys Ile Cys Leu Val Cys Leu<br>            260                   265               270 | 816 |
| gac gcg cca gga ggg ctg gag ctc agc gac acc cac agg gca ctc cag<br>Asp Ala Pro Gly Gly Leu Glu Leu Ser Asp Thr His Arg Ala Leu Gln<br>            275                   280               285 | 864 |
| ctc ctt cac ggc gga ggc tac agc aag aac ggg gcc aat cgc tgg tac<br>Leu Leu His Gly Gly Gly Tyr Ser Lys Asn Gly Ala Asn Arg Trp Tyr<br>290                     295               300 | 912 |
| gac aag tcc ctg cag ttt gtg gtg ggc cga gac ggc acc tgc ggt gtg<br>Asp Lys Ser Leu Gln Phe Val Val Gly Arg Asp Gly Thr Cys Gly Val<br>305                     310               315               320 | 960 |
| gtg tgc gaa cac tcc cca ttc gat ggc atc gtc ctg gtg cag tgc act<br>Val Cys Glu His Ser Pro Phe Asp Gly Ile Val Leu Val Gln Cys Thr<br>                 325                   330               335 | 1008 |
| gag cat ctg ctc aag cac atg acg cag agc agc agg aag ctg atc cga<br>Glu His Leu Leu Lys His Met Thr Gln Ser Ser Arg Lys Leu Ile Arg | 1056 |

-continued

```
                     340                 345                 350
gca gac tcc gtc agc gag ctc ccc gcc ccc cgg agg ctg cgg tgg aaa       1104
Ala Asp Ser Val Ser Glu Leu Pro Ala Pro Arg Arg Leu Arg Trp Lys
            355                 360                 365 tgc tcc ccg gaa att caa ggc cac tta gcc tcc tcg gca gaa aaa ctt       1152
Cys Ser Pro Glu Ile Gln Gly His Leu Ala Ser Ser Ala Glu Lys Leu
370                 375                 380 caa cga ata gta aag aac ctt gac ttc att gtc tat aag ttt gac aac       1200
Gln Arg Ile Val Lys Asn Leu Asp Phe Ile Val Tyr Lys Phe Asp Asn
        385                 390                 395                 400 tat ggg aaa aca ttc att aag aag cag aaa tcc agc cct gat gcc ttc       1248
Tyr Gly Lys Thr Phe Ile Lys Lys Gln Lys Ser Ser Pro Asp Ala Phe
                405                 410                 415 atc cag gtg gcc ctc cag ctg gcc ttc tac agg ctc cac cga aga ctg       1296
Ile Gln Val Ala Leu Gln Leu Ala Phe Tyr Arg Leu His Arg Arg Leu
            420                 425                 430 gtg ccc acc tac gag agc gcg tcc atc cgc cga ttc cag gag gga cgc       1344
Val Pro Thr Tyr Glu Ser Ala Ser Ile Arg Arg Phe Gln Glu Gly Arg
        435                 440                 445 ctg gac aac atc aga tcg gcc act cca gag gca ctg gct ttt gtg aga       1392
Leu Asp Asn Ile Arg Ser Ala Thr Pro Glu Ala Leu Ala Phe Val Arg
    450                 455                 460 gcc gtg act gac cac aag gct gct gtg cca gct tct gag aag ctt ctg       1440
Ala Val Thr Asp His Lys Ala Ala Val Pro Ala Ser Glu Lys Leu Leu
465                 470                 475                 480 ctc ctg aag gat gcc atc cgt gcc cag act gca tac aca gtc atg gcc       1488
Leu Leu Lys Asp Ala Ile Arg Ala Gln Thr Ala Tyr Thr Val Met Ala
                485                 490                 495 ata aca ggg atg gcc att gac aac cac ctg ctg gca ctg cgg gac gtg       1536
Ile Thr Gly Met Ala Ile Asp Asn His Leu Leu Ala Leu Arg Asp Val
            500                 505                 510 gcc cgg gcc atg tgc aag gag ctg ccc gag atg ttc atg gat gaa acc       1584
Ala Arg Ala Met Cys Lys Glu Leu Pro Glu Met Phe Met Asp Glu Thr
        515                 520                 525 tac ctg atg agc aac cgg ttt gtc ctc tcc act agc cag gtg ccc aca       1632
Tyr Leu Met Ser Asn Arg Phe Val Leu Ser Thr Ser Gln Val Pro Thr
    530                 535                 540 acc atg gaa atg ttc tgc tgt tat ggt cct gtg gtc cca aat ggg tat       1680
Thr Met Glu Met Phe Cys Cys Tyr Gly Pro Val Val Pro Asn Gly Tyr
545                 550                 555                 560 ggt gcc tgc tac aac ccc cag cca gag acc atc ctt ttc tgc atc tct       1728
Gly Ala Cys Tyr Asn Pro Gln Pro Glu Thr Ile Leu Phe Cys Ile Ser
                565                 570                 575 agc ttt cac agc tgc aaa gag act tct tct agc aag ttt gca aaa gct       1776
Ser Phe His Ser Cys Lys Glu Thr Ser Ser Ser Lys Phe Ala Lys Ala
            580                 585                 590 gtg gaa gaa agc ctc att gac atg aga gac ctc tgc agt ctg ctg ccg       1824
Val Glu Glu Ser Leu Ile Asp Met Arg Asp Leu Cys Ser Leu Leu Pro
        595                 600                 605 cct act gag agc aag cca ttg gca aca aag gaa aaa gcc acg agg ccc       1872
Pro Thr Glu Ser Lys Pro Leu Ala Thr Lys Glu Lys Ala Thr Arg Pro
    610                 615                 620 agc cag gga cac caa cct tga                                           1893
Ser Gln Gly His Gln Pro
625                 630

<210> SEQ ID NO 4
<211> LENGTH: 630
<212> TYPE: PRT
<213> ORGANISM: Homo sapiens
```

```
<400> SEQUENCE: 4

Met Ala Ala Lys Thr Pro Ser Ser Glu Glu Ser Gly Leu Pro Lys Leu
1               5                   10                  15

Pro Val Pro Pro Leu Gln Gln Thr Leu Ala Thr Tyr Leu Gln Cys Met
            20                  25                  30

Arg His Leu Val Ser Glu Glu Gln Phe Arg Lys Ser Gln Ala Ile Val
        35                  40                  45

Gln Gln Phe Gly Ala Pro Gly Gly Leu Gly Glu Thr Leu Gln Gln Lys
    50                  55                  60

Leu Leu Glu Arg Gln Glu Lys Thr Ala Asn Trp Val Ser Glu Tyr Trp
65                  70                  75                  80

Leu Asn Asp Met Tyr Leu Asn Asn Arg Leu Ala Leu Pro Val Asn Ser
                85                  90                  95

Ser Pro Ala Val Ile Phe Ala Arg Gln His Phe Pro Gly Thr Asp Asp
            100                 105                 110

Gln Leu Arg Phe Ala Ala Ser Leu Ile Ser Gly Val Leu Ser Tyr Lys
        115                 120                 125

Ala Leu Leu Asp Ser His Ser Ile Pro Thr Asp Cys Ala Lys Gly Gln
    130                 135                 140

Leu Ser Gly Gln Pro Leu Cys Met Lys Gln Tyr Tyr Gly Leu Phe Ser
145                 150                 155                 160

Ser Tyr Arg Leu Pro Gly His Thr Gln Asp Thr Leu Val Ala Gln Asn
                165                 170                 175

Ser Ser Ile Met Pro Glu Pro Glu His Val Ile Val Ala Cys Cys Asn
            180                 185                 190

Gln Phe Phe Val Leu Asp Val Val Ile Asn Phe Arg Arg Leu Ser Glu
        195                 200                 205

Gly Asp Leu Phe Thr Gln Leu Arg Lys Ile Val Lys Met Ala Ser Asn
    210                 215                 220

Glu Asp Glu Arg Leu Pro Pro Ile Gly Leu Leu Thr Ser Asp Gly Arg
225                 230                 235                 240

Ser Glu Trp Ala Glu Ala Arg Thr Val Leu Val Lys Asp Ser Thr Asn
                245                 250                 255

Arg Asp Ser Leu Asp Met Ile Glu Arg Cys Ile Cys Leu Val Cys Leu
            260                 265                 270

Asp Ala Pro Gly Gly Leu Glu Leu Ser Asp Thr His Arg Ala Leu Gln
        275                 280                 285

Leu Leu His Gly Gly Gly Tyr Ser Lys Asn Gly Ala Asn Arg Trp Tyr
    290                 295                 300

Asp Lys Ser Leu Gln Phe Val Val Gly Arg Asp Gly Thr Cys Gly Val
305                 310                 315                 320

Val Cys Glu His Ser Pro Phe Asp Gly Ile Val Leu Val Gln Cys Thr
                325                 330                 335

Glu His Leu Leu Lys His Met Thr Gln Ser Ser Arg Lys Leu Ile Arg
            340                 345                 350

Ala Asp Ser Val Ser Glu Leu Pro Ala Pro Arg Arg Leu Arg Trp Lys
        355                 360                 365

Cys Ser Pro Glu Ile Gln Gly His Leu Ala Ser Ala Glu Lys Leu
    370                 375                 380

Gln Arg Ile Val Lys Asn Leu Asp Phe Ile Val Tyr Lys Phe Asp Asn
385                 390                 395                 400

Tyr Gly Lys Thr Phe Ile Lys Lys Gln Lys Ser Ser Pro Asp Ala Phe
```

-continued

```
                      405                 410                 415
Ile Gln Val Ala Leu Gln Leu Ala Phe Tyr Arg Leu His Arg Arg Leu
                420                 425                 430
Val Pro Thr Tyr Glu Ser Ala Ser Ile Arg Arg Phe Gln Glu Gly Arg
            435                 440                 445
Leu Asp Asn Ile Arg Ser Ala Thr Pro Glu Ala Leu Ala Phe Val Arg
        450                 455                 460
Ala Val Thr Asp His Lys Ala Ala Val Pro Ala Ser Glu Lys Leu Leu
465                 470                 475                 480
Leu Leu Lys Asp Ala Ile Arg Ala Gln Thr Ala Tyr Thr Val Met Ala
                485                 490                 495
Ile Thr Gly Met Ala Ile Asp Asn His Leu Leu Ala Leu Arg Asp Val
                500                 505                 510
Ala Arg Ala Met Cys Lys Glu Leu Pro Glu Met Phe Met Asp Glu Thr
            515                 520                 525
Tyr Leu Met Ser Asn Arg Phe Val Leu Ser Thr Ser Gln Val Pro Thr
        530                 535                 540
Thr Met Glu Met Phe Cys Cys Tyr Gly Pro Val Val Pro Asn Gly Tyr
545                 550                 555                 560
Gly Ala Cys Tyr Asn Pro Gln Pro Glu Thr Ile Leu Phe Cys Ile Ser
                565                 570                 575
Ser Phe His Ser Cys Lys Glu Thr Ser Ser Lys Phe Ala Lys Ala
                580                 585                 590
Val Glu Glu Ser Leu Ile Asp Met Arg Asp Leu Cys Ser Leu Leu Pro
            595                 600                 605
Pro Thr Glu Ser Lys Pro Leu Ala Thr Lys Glu Lys Ala Thr Arg Pro
        610                 615                 620
Ser Gln Gly His Gln Pro
625                 630

<210> SEQ ID NO 5
<211> LENGTH: 25
<212> TYPE: DNA
<213> ORGANISM: Artificial
<220> FEATURE:
<223> OTHER INFORMATION: PCR primer designed from human and rat
      sequences

<400> SEQUENCE: 5
gccatggctt cccatgtgga aggac                                          25

<210> SEQ ID NO 6
<211> LENGTH: 27
<212> TYPE: DNA
<213> ORGANISM: Artificial
<220> FEATURE:
<223> OTHER INFORMATION: PCR primer based on human and rat sequences

<400> SEQUENCE: 6
gggtcattgt aarttatctt cagtccc                                        27
```

HUMAN HIGH AFFINITY CHOLINE TRANSPORTER

PRIORITY

This application is a divisional of U.S. Ser. No. 10/271,090 filed Oct. 15, 2002, which is a divisional of U.S. Ser. No. 09/657,252, filed Sep. 7, 2000, now U.S. Pat. No. 6,500,643, all of which are incorporated by reference in their entirety.

GOVERNMENT INTERESTS

This invention was made with Government support under Grant Number R03 AG015688 awarded by the National Institute of Aging. The Government has certain rights in the invention.

FIELD OF THE INVENTION

The invention relates to human high affinity choline transporter polynucleotides, polypeptides and their uses.

BACKGROUND OF THE INVENTION

The cholinergic transmissions or neuromodulations in the central nervous system are involved in a number of fundamental brain processes such as learning and memory (Aigner & Mishkin, *Behav. & Neural. Biol.* 45:81-87 (1986); Fibinger, TINS, 14:220-223 (1991)), arousal, and sleep-wake cycles (Karczmar, in Biology of Cholinergic Function, (eds A.M. Goldberg & I. Hanin) Raven Press, N.Y. 1976, pp 395-449; Fibinger, 1991). In this system, the formation of the neurotransmitter acetylcholine is catalyzed by the enzyme choline acetyltransferase (ChAT, E.C. 2.3.1.6), which transfers an acetyl group from acetylcoenzyme A to choline, in the presynaptic nerve terminals of cholinergic neurons. Acetylcholine is packaged into the synaptic vesicles by a vesicular acetylcholine transporter (VAChT) and is then ready to be released in a calcium dependent manner. Acetylcholine binds specifically to either the nicotinic or muscarinic receptors (AChR) to transmit information to the postsynaptic neurons. The action of acetylcholine is terminated through hydrolysis to acetate and choline by the enzyme acetylcholinesterase (ACHE, E.C.3.1.1.7). Most of the choline is then transported back to the presynaptic terminal to be recycled as one of the precursors for the biosynthesis of acetylcholine. This step, which is mediated by the action of the high affinity choline transporter (HACT), is believed to be the rate limiting step of the biosynthesis of the neurotransmitter acetylcholine, which plays a pivotal role in processes such as learning, memory, and sleep (Karczmar, 1976; Figinger, 1991).

Altered functioning of the cholinergic system has been observed during normal aging processes (Cohen et al., JAMA, 274:902-7 (1995); Smith et al., *Neurobiol Aging*, 16: 161-73 (1995)), while its dysfunction underlies nicotine addiction and a number of neurological and psychiatric disorders most notably Alzheimer's disease (AD), Myasthenia Gravis, Amyotrophic Lateral Sclerosis (ALS), and epilepsies. Clearly, molecular cloning of these cholinergic components are important in the understanding of the cholinergic mechanism and neurotransmission in the central nervous system during normal aging processes and under certain disease states such as AD and ALS. So far, all the components but one have been cloned. The cloned molecules include biosynthetic enzyme choline acetyltransferase (ChAT), vesicular acetylcholine transporter (VAChT), both muscarinic and nicotinic type acetylcholine receptors (AChR), and acetylcholinesterase (AChE). The availability of these agents or tools has advanced cholinergic research tremendously which has led to more insights and knowledge on how cholinergic systems function. However, the sodium-dependent high affinity choline transporter (HACT), which is believed to be the rate limiting step for the neurotransmitter biosynthesis and regeneration has not yet been cloned. In order to obtain a more thorough understanding about how the cholinergic mechanism operates in the central nervous system and how cholinergic neurotransmissions and modulations are regulated at the molecular level, the high affinity choline transporter must be cloned.

In the cholinergic nerve synaptosome preparations, two types of choline uptake systems have been described (Yamamura & Snyder, *J. Neurochem.* 21:1355-1374 (1973); Haga & Noda, *Biochem. Biophys. Acta,* 291:564-575 (1973); Jope, *Brain Res. Rev.* 1, 313-344 (1979)), one of which uses sodium as electrogenic driving force and is of high affinity for choline with an apparent Km less than 10 μM (HACT). Choline transporting activity of this type of uptake system is associated with efficient conversion of choline to acetylcholine and choline transporting activity is inhibited by low concentrations of hemicholinium-3 (Ki=25 to 100 nM). While the other uptake system does not depend on sodium, it exhibits a lower affinity for choline with an apparent Km between 40 to 100 μM (low affinity choline transporter, LACT), and is hemicholinium-3 insensitive. Studies over the last two decades indicate that the high affinity choline uptake system is coupled either physically (Barker & Mittag, *J. Pharmacol. Exp. Ther.* 192:86-94 (1975)) or kinetically (Jope & Jenden, *Life Sci.* 20:1398-92 (1977)) to the biosynthesis of the neurotransmitter acetylcholine. In vivo pharmacological studies conducted by Kuhar and his colleagues suggest that the high affinity choline transporter may play a regulatory role in addition to the rate limiting step in acetylcholine biosynthesis (Kuhar & Murrin, *J. Neurochem.* 30:15-21 (1978)). Phospholipase A2 and cAMP pathways were reported to act synergistically to regulate high affinity choline transporter activity (Cancela et al., *Biochem. Biophys. Res. Commun.* 213:944-949 (1995); Vogelsberg et al., *J. Neurochem.* 68:1062-70 (1997)).

Recently, age-related alterations in the density of cholinergic reuptake sites were examined in discrete brain regions of behaviorally tested rats using autoradiography. A strong correlation was found between behavioral performance of aged rats and density of the binding sites for hemicholinium-3 in dorsal hippocampal subfield CA3 and dentate gyrus (Smith et al., *Neurobiol Aging.* 16:161-73 (1995)). Similarly, a 3 to 4 fold decreased brain choline uptake in normal, older human adults was reported using an in vivo proton magnetic resonance spectroscopy, indicating uptake of circulating choline into the brain decreases with age (Cohen et al., JAMA, 274:902-7 (1995)). Interestingly, an increase in high affinity choline transport was observed in the cortical brain region of Alzheimer's patients, suggesting disordered regulation of this rate limiting component of acetylcholine synthesis is above and beyond that required to compensate for the reduced cholinergic synaptic functionality (Bissette et al., *Ann. N.Y. Acad. Sci.,* 777:197-204 (1996)). Undoubtedly, isolation of the high affinity choline transporter gene would allow the mechanism of transport to be studied at the molecular level and could provide further insights to its function and regulation under normal and pathological conditions.

So far, attempts using various strategies to purify and isolate a high affinity choline transporter gene have not been successful (for a recent review on this topic, see Happe & Murrin, *J. Neurochem.* 60:1191-1201 (1993)). Isolation and purification of a transporter molecule using biochemical methods have been difficult partly due to fact that the transporter is present in low amounts and becomes unstable in later stages of purification (Rylett, *J. Neurochem.* 51:1942-5 (1988)). Limited biochemical characterization of HACT has revealed proteins with molecular sizes of 42, 58, and 90 kDa, which were labeled with tritiated choline mustard aziridinium ion from a Torpedo electric organ membrane preparation (Rylett, 1988). An 80 kDa protein from locust head ganglia has been labeled with tritiated hemicholinium-3 and isolated by usage of a monoclonal antibody that blocks HACT activity (Knipper et al., *FEBS Lett.* 245:235-237 (1989); Knipper, *Neurochem. Int.* 14:211-215(1989)). The polypeptide is capable of accumulating choline into liposomes, is hemicholinium-3 sensitive, and has the same ionic and energy requirements as HACT from other sources (Knipper et al., *Biochem. Biophys. Acta,* 1065:107-113 (1991)). Further purification yields a protein with an apparent molecular size of 90 kDa which becomes a 65 kDa protein upon treatment by endoglycosidase F (Knipper et al., 1991). These results suggest that at least, in the locust, the HACT molecule is a single polypeptide, although whether the functional HACT requires multiple subunits is not clear.

A second approach of cloning HACT using an *Xenopus oocyte* expression system has been explored by several laboratories (O'Regan et al., *Mol. Brain. Res.* 32:135-42 (1994)). Hemicholinium-3 sensitive HACT activity could be induced upon introduction of fractionated mRNAs from Torpedo electric lobe tissues (O'Regan et al., 1994). However, a truncated synaptotagmin C2 domain was found to be responsible for this HACT activity while full length synaptotagmin is not capable of this action (O'Regan et al., 1994). It is not clear what this finding means, nonetheless, it did point out that the endogenous choline transporter activity in *Xenopus oocyte* could obscure the signal generated by the cDNAs. Another approach based on homology cloning strategy has also been attempted without success. In the last six years, several neurotransmitter transporters have been cloned, including those for norepinephrine, dopamine, serotonin, gama-aminobutyric acid (GABA), glycine, and proline (Amara & Kuhar, *Annu. Rev. Neurosci.* 16:73-94 (1993); Malandro & Kilberg, *Annu. Rev. Biochem.* 65:305-36 (1996)). All of the transporters appear to belong to a single family of proteins of approximately 600-700 amino acids and have 12 membrane spanning domains. One would anticipate HACT to be one member of this family although it is possible that a unique or a significantly different structure is required by HACT. Homology cloning of a choline transporter based on the conserved regions of this family was claimed, but later this molecule was identified as the creatine transporter (Mayser et al., *FEBS Lett.* 305:31-36 (1992). Thus it appears a search for alternative approach to clone HACT is fully warranted and desirable.

SUMMARY OF THE INVENTION

The invention provides human high affinity choline transporter polynucleotides and polypeptides and compositions comprising human high affinity choline transporter polynucleotides and polypeptides. The invention also provides vectors and recombinant host cells comprising human high affinity choline transporter polynucleotides and polypeptides. Additionally, the invention provides methods for identifying test agents that decrease or increase high affinity choline transporter protein activity and for identifying binding partners of high affinity choline transporter polypeptides. These and other uses/embodiments of the invention are provided by one or more of the embodiments described below.

One embodiment of the invention provides an isolated high affinity choline transporter protein which has the amino acid sequence shown in SEQ ID NO:2, and naturally occurring biologically active variants thereof.

Another embodiment of the invention provides an isolated polypeptide that comprises about at least six contiguous amino acids of a high affinity choline transporter as shown in SEQ ID NO:2.

A further embodiment of the invention provides a composition comprising a high affinity choline transporter protein as shown in SEQ ID NO:2 or a polypeptide comprising about at least six contiguous amino acids of a high affinity choline transporter as shown in SEQ ID NO:2 and a pharmaceutically acceptable carrier. The composition can optionally comprise a choline acetyltransferase polypeptide.

Still another embodiment of the invention provides an antibody or antigen binding portion thereof that specifically binds to a high affinity choline transporter polypeptide as shown in SEQ ID NO:2.

Yet another embodiment of the invention provides an isolated polynucleotide which encodes a high affinity choline transporter protein as shown in SEQ ID NO:2. The polynucleotide can comprise the sequence shown in SEQ ID NO: 1. The polynucleotide can be present in a vector, and the vector can in turn be present in a recombinant host cell.

Even another embodiment of the invention provides a polynucleotide comprising about at least 12 contiguous nucleic acids of a polynucleotide as shown in SEQ ID NO: 1.

Another embodiment of the invention provides a composition comprising a polynucleotide which encodes a high affinity choline transporter polypeptide as shown in SEQ ID NO:2 or a polynucleotide that comprises the sequence shown in SEQ ID NO: 1 and a pharmaceutically acceptable carrier.

Still another embodiment of the invention provides a method of screening test agents for the ability to decrease or increase high affinity choline transporter protein activity. A first host cell comprising about at least 12 contiguous nucleic acids of a polynucleotide as shown in SEQ ID NO: 1 is contacted with a test agent and choline. A second host cell comprising about at least 12 contiguous nucleic acids of a polynucleotide as shown in SEQ ID NO: 1 is contacted with choline. The amount of choline that is transported into the first cell and the second cell is measured and the amounts of choline transported into the first cell and into the second cell are compared. A test agent that decreases the amount of choline transported into the first cell as compared to the second cell is a potential drug for decreasing high affinity choline transporter protein activity, and a test agent that increases the amount of choline transported into the first cell as compared to the second cell is a potential drug for increasing high affinity choline transporter protein activity.

Yet another embodiment of the invention provides a method for identifying a binding partner of a polypeptide that comprises about at least six contiguous amino acids of a high affinity choline transporter as shown in SEQ ID NO:2. The polypeptide is contacted with a candidate binding partner. Whether the binding partner binds to the polypeptide is determined.

The invention therefore provides for the first time human HACT polynucleotides, polypeptides, compositions, and uses thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
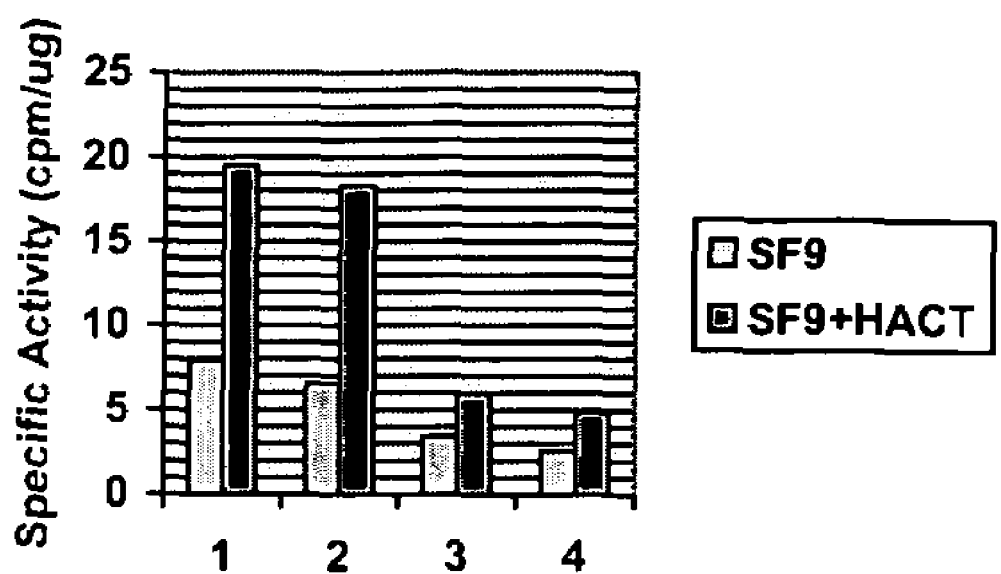
FIG. 1 shows the relative activity of recombinant human high affinity choline transporter in SF9 cells.

Polypeptides of the invention Polypeptides of the invention comprise high affinity choline transporter polypeptides, which are preferably mammalian polypeptides, such as human high affinity choline transporter polypeptides. Polypeptides of the invention also comprise choline acetyltransferase polypeptides, which preferably comprise a mammalian polypeptide such as a human, mouse, pig, or bovine choline acetyltransferase polypeptide. Polypeptides of the invention can either be full-length polypeptides or fragments of polypeptides. For example, fragments of polypeptides can comprise about 6, 10, 25, 50, 100, 200, 250, or 500 amino acids of polypeptides of the invention. Examples of polypeptides of the invention include human high affinity choline transporter and choline acetyltransferase as shown in SEQ ID NO:2 and SEQ ID NO:4, respectively. Homologous amino acid sequences which are at least about 50, preferably about 75, 90, 96, 98, or 99% identical to the polypeptide sequences shown in SEQ ID NO:2 and SEQ ID NO:4, are also human high affinity choline transporter and choline acetyltransferase polypeptides.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing. Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Polypeptides of the invention further comprise biologically functional equivalents of at least about 6, 10, 25, 50, 100, 200, 250, or 500 amino acids of the polypeptides shown in SEQ ID NO:2 or SEQ ID NO:4. A polypeptide is a biological equivalent if it reacts about the same to a polypeptide of the invention in an assay such as an immunohistochemical assay, an enzyme-linked immunosorbent assay (ELISA), an radioimmunoassay (RIA), or a western blot assay. Preferably, the assay is a competition assay wherein the biologically equivalent polypeptide is capable of reducing binding of the polypeptide shown in SEQ ID NO:2 or SEQ ID NO:4, or a fragment thereof, to a corresponding reactive antigen or antibody by about 80, 95, 99, or 100%.

The biological activity of a high affinity choline transporter polypeptide or a high affinity choline transporter polypeptide in combination with a choline acetyltransferase polypeptide can be measured by expression of the polypeptides in *Xenopus oocytes*. See e.g. Kanai & Hediger, *Nature*, 360:467 (1992); Okuda et al. *Nat. Neurosci.* 3:120-5 (2000). Briefly, SP6 or T7 RNA polymerase in the presence of cap analog can be used to prepare cRNA in vitro. Stage V to VI *Xenopus laevis* oocytes can be injected with 20-30 ng of capped cRNA. Choline uptake can be measured 2 to 3 days after injection by incubating 6-8 oocytes for 30-45 minutes with [$^3$H] choline chloride in 750 µl standard medium (100 mM NaCl, 2 mM KCl, 1 mM MgCl$_2$, 10 mM HEPES, 5 mM Tris, pH 7.4). Oocytes are solublized with 10% SDS and the [$^3$H] content measured by liquid scintillation counting.

Optionally, the biological activity of a high affinity choline transporter polypeptide or a high affinity choline transporter polypeptide in combination with a choline acetyltransferase polypeptide can be measured by transfecting or infecting cells with a vector comprising a coding sequence for a high affinity choline transporter polypeptide, optionally in combination with a coding sequence for a choline acetyltransferase polypeptide. Cells can also be transfected or infected with 2 vectors wherein one vector comprises a coding sequence for a high affinity choline transporter polypeptide and a second vector comprises a coding sequence for a choline acetyltransferase polypeptide. Any type of prokaryotic or eukaryotic cells can be used including mammalian, bacterial, yeast, and insect cells. A population of the cells can be incubated with labeled choline, such as tritiated choline chloride, and Hemicholinium-3. The cells are pelleted, washed, and solubilized in NaOH. The tritium content can be determined by liquid scintillation counting.

Preferably, a polypeptide of the invention is produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Preferably, the polypeptide is isolated from the membrane of the host cell or a protein fraction of the host cell. Optionally, a polynucleotide encoding a polypeptide can be translated in a cell-free translation system.

If desired, a polypeptide can be produced as a fusion protein, which can also contain other amino acid sequences, such as amino acid linkers or signal sequences, as well as ligands useful in protein purification, such as glutathione- S-transferase, green fluorescent protein (GFP), red fluorescent protein (RFP), histidine tag, and staphylococcal protein A. More than one polypeptide of the invention can be present in a fusion protein.

Polynucleotides of the Invention

Polynucleotides of the invention contain less than an entire genome and can be RNA or single- or double-stranded DNA. Preferably, the polynucleotides are isolated and purified free of other components, such as proteins and lipids. The polynucleotides of the invention encode the polypeptides described above. Polynucleotides of the invention can also comprise other nucleotide sequences, such as sequences coding for linkers, signal sequences, heterologous signal sequences, TMR stop transfer sequences, transmembrane domains, or ligands useful in protein detection and purification such as glutathione-S-transferase, GFP, RFP, histidine tag, and staphylococcal protein A.

Degenerate nucleotide sequences encoding the polypeptides of the invention, as well as homologous nucleotide sequences which are at least about 50, preferably about 75, 90, 96, 98, or 99% identical to the nucleotide sequences shown in SEQ ID NO: 1 and SEQ ID NO:3, and the complements thereof are also polynucleotides of the invention. Percent sequence identity can be calculated as described in the "Polypeptides" section. Complementary DNA (cDNA) molecules, species homologs, and variants of polynucleotides which encode biologically active high affinity choline transporter and choline acetyltransferase polypeptides also are polynucleotides of the invention. Preferably, a polynucleotide of the invention comprises about 5, 10, 12, 15, 50, 100, 500, or 900 nucleotides of a nucleic acid sequence as shown in SEQ ID NO:1 and SEQ ID NO:3.

Polynucleotides of the invention can be isolated from nucleic acid molecules present in, for example, a biological sample, such as spinal fluid or brain tissue. Polynucleotides can also be synthesized in the laboratory, for example, using an automatic synthesizer. An amplification method such as PCR can be used to amplify polynucleotides from either genomic DNA or cDNA encoding polypeptides of the invention.

Polynucleotides of the invention can comprise coding sequences for naturally occurring polypeptides or can encode altered sequences which do not occur in nature. If desired, polynucleotides can be cloned into an expression vector comprising, for example, promoters, enhancers, or other regulatory elements that drive expression of the polynucleotides of the invention in host cells. An expression vector can be, for example, a plasmid, such as pBR322, pUC, or Co1E1, or an adenovirus vector, such as an adenovirus Type 2 vector or Type 5 vector. Optionally, other vectors can be used, including but not limited to Sindbis virus, simian virus 40, alphavirus vectors, poxvirus vectors, baculovirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

A vector comprising a polynucleotide of the invention can be transformed into, for example, bacterial, yeast, insect, or mammalian cells so that the polypeptides of the invention can be expressed in and isolated from cell culture. Any of those techniques which are available in the art can be used to introduce polynucleotides into the host cells. These include, but are not limited to, transfection with naked or encapsulated nucleic acids, cellular fusion, protoplast fusion, viral infection, and electroporation.

Polynucleotides of the invention can be used, for example, as probes or primers to detect the presence of high affinity choline transporter polynucleotides in a sample, such as a biological sample. The ability of such probes to specifically hybridize to polynucleotide sequences will enable them to be of use in detecting the presence of complementary sequences in a given sample. Polynucleotide probes of the invention can hybridize to complementary sequences in a sample such as a biological sample, for example, brain tissue or spinal fluid, thereby detecting the presence or absence of human high affinity transporter polynucleotides in samples. Polynucleotides from the sample can be, for example, subjected to gel electrophoresis or other size separation techniques or can be dot blotted without size separation. The polynucleotide probes are preferably labeled. Suitable labels, and methods for labeling probes are known in the art, and include, for example, radioactive labels incorporated by nick translation or by kinase, biotin, fluorescent probes, and chemiluminescent probes. The polynucleotides from the sample are then treated with the probe under hybridization conditions of suitable stringencies.

Depending on the application, varying conditions of hybridization can be used to achieve varying degrees of selectivity of the probe towards the target sequence. For applications requiring high selectivity, relatively stringent conditions can be used, such as low salt and/or high temperature conditions, such as provided by a salt concentration of from about 0.02 M to about 0.15 M at temperatures of from about 50° C. to about 70° C. For applications requiring less selectivity, less stringent hybridization conditions can be used. For example, salt conditions from about 0.14 M to about 0.9 M salt, at temperatures ranging from about 20° C. to about 55° C. The presence of a hybridized complex comprising the probe and a complementary polynucleotide from the sample indicates the presence of the microbe or polynucleotide sequence in the sample.

Antibodies

Antibodies of the invention are antibody molecules that specifically and stably bind to a polypeptide of the invention or fragment thereof. An antibody of the invention can be a polyclonal antibody, a monoclonal antibody, a single chain antibody (scFv), or a binding portion of an antibody. Such binding portions include, for example, Fab fragments, F(ab')$_2$ fragments, and Fv fragments. These antibody fragments can be made by conventional procedures, such as proteolytic fragmentation procedures, as described in J. Goding, *Monoclonal Antibodies: Principles and Practice*, pp. 98-118 (N.Y. Academic Press 1983).

Antibodies can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antibodies are known in the art.

Additionally, monoclonal antibodies directed against an epitope present on a polypeptide of the invention can also be readily produced. An epitope can be a linear, sequential epitope or a conformational epitope. Epitopes within a polypeptide of the invention can be identified by several methods. See, e.g., U.S. Pat. No. 4,554,101; Jameson & Wolf, CABIOS 4:181-186 (1988). For example, a polypeptide of the invention can be isolated and screened. A series of short peptides, which together span the entire polypeptide sequence, can be prepared by proteolytic cleavage. By starting with, for example, 100-mer polypeptide fragments, each fragment can be tested for the presence of epitopes recognized in an ELISA. For example, in an ELISA assay a polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific adsorbtion is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

Monoclonal antibodies directed against epitopes present on a polypeptide of the invention can be produced by fusing normal B cells from a mammal, such as a mouse, immunized with polypeptide of the invention with, for example, HAT-sensitive mouse myeloma cells to produce hybridomas. Hybridomas producing polypeptide-specific antibodies can be identified using RIA or ELISA and isolated by cloning in semi-solid agar or by limiting dilution. Clones producing polypeptide-specific antibodies are isolated by another round of screening. Techniques for producing and processing monoclonal antibodies are known in the art.

Antibodies, either monoclonal and polyclonal, which are directed against the polypeptides of the invention, are particularly useful for detecting the presence of high affinity choline transporter or choline acetyltransferase antigens in a sample, such as a biological sample from a human. An immunoassay for an antigen may utilize one antibody or several antibodies. An immunoassay for an antigen may use, for example, a monoclonal antibody directed towards an epitope, a combination of monoclonal antibodies directed towards epitopes of one polypeptide, monoclonal antibodies directed towards epitopes of different polypeptides, polyclonal antibodies directed towards the same antigen, polyclonal antibodies directed towards different antigens, or a combination of monoclonal and polyclonal antibodies. Immunoassay protocols may be based, for example, upon competition, direct reaction, or sandwich type assays using, for example, labeled antibody. Immunoassays to detect and/or quantify antibodies, include for example, direct binding assays such as RIA or ELISA assays. The labels can be, for example, fluorescent, chemiluminescent, or radioactive.

The polyclonal or monoclonal antibodies may further be used to isolate high affinity choline transporter antigens by immunoaffinity columns. The antibodies can be affixed to a solid support by, for example, adsorbtion or by covalent linkage so that the antibodies retain their immunoselective activity. Optionally, spacer groups may be included so that the antigen binding site of the antibody remains accessible. The immobilized antibodies can then be used to bind antigens from a sample, such as a biological sample or a cell culture, wherein the cells express a polynucleotide of the invention. The bound antigens are recovered from the column matrix by, for example, a change in pH. Antibodies of the invention can also be used in immunolocalization studies to analyze the presence and distribution of a polypeptide of the invention during various cellular events or physiological conditions.

Antibodies of the invention can be used to visualize the amount and location of HACT polypeptides in vitro and in vivo. The amount and location of HACT polypeptides in a patient or biological sample can be used to diagnose such diseases as pain, spasticity, myoclonus, muscle spasm, muscle hyperactivity, epilepsy, stroke, head trauma, neuronal cell death, multiple sclerosis, spinal cord injury, dystonia, Alzheimer's disease, Myasthenia Gravis, multi-infarct dementia, AIDS dementia, Parkinson's disease, Huntington's disease, amyotrophic lateral sclerosis (ALS), attention deficit disorder, organic brain syndromes, schizophrenia, nicotine addiction, and memory or cognitive disorders. The amount and location of HACT polypeptides can be compared to the amount and location of HACT polypeptides in patients without these diseases in order to make the diagnosis. For example, antibodies to an extracellular portion of a HACT polypeptide can be labeled with, for example, a non-radioactive isotope and delivered in vivo to a mammalian subject, such as a rabbit, rat, mouse, guinea pig, chimpanzee, macaque, or human. The labeled antibodies will bind to HACT polypeptides and the quantity and location of HACT polypeptides in the patient can be visualized using for example, nuclear magnetic resonance imaging or magnetic resonance imaging.

Methods of Screening Test Agents

The identification of agents or compounds that enhance or inhibit the activity of a high affinity choline transporter or a combination of a high affinity choline transporter and a choline acetyltransferase is important for the development of drugs useful in the treatment of neurological conditions and disorders including, but not limited to pain, spasticity, myoclonus, muscle spasm, muscle hyperactivity, epilepsy, stroke, head trauma, neuronal cell death, multiple sclerosis, spinal cord injury, dystonia, Alzheimer's disease, Myasthenia Gravis, multi-infarct dementia, AIDS dementia, Parkinson's disease, Huntington's disease, amyotrophic lateral sclerosis (ALS), attention deficit disorder, organic brain syndromes, schizophrenia, nicotine addiction, and memory or cognitive disorders. The present invention provides materials and methods that are suitable for such screening. A host cell can be transformed with a high affinity choline transporter polynucleotide optionally in combination with a choline acetyltransferase polynucleotide. A host cell can be any prokaryotic or eukaryotic cell including, for example, mammalian, bacterial, yeast, or insect cells. Preferably, the high affinity choline transporter and choline acetyltransferase polynucleotides are heterologous to the cell. Such transformed cells can form stable lines that constitutively or inductively express a high affinity choline transporter polypeptide, optionally in combination with a choline acetyltransferase polypeptide. Such transfected cells are useful for screening assays to determine whether a candidate agent has characteristics of enhancing or inhibiting choline transport.

A method for the analysis or screening of an agent for treatment, prevention, or amelioration of a disease or condition associated with a nervous system disorder comprises culturing separately first and second host cells, wherein the first and second host cells are preferably of the same species, and more preferably of the same strain, wherein the first and second host cells comprise a polynucleotide encoding a high affinity choline transporter, optionally in combination with a polynucleotide encoding choline acetyltransferase. The first host cell is contacted with an agent, which is preferably a compound, such as a peptide or an organic compound, or a composition or mixture, in the presence of choline. Preferably, the choline is labeled with, for example, a radioisotope. The first host cell is then tested for enhancement or inhibition of choline transport into the first host cell as compared to choline transport into the second host cell which was not contacted with the agent (i.e., the control cell).

An agent is an enhancer of choline transport uptake if the amount of intracellular labeled choline is greater in the agent-contacted host cell than in the non-agent-contacted host cell. Conversely, an agent is an inhibitor of choline transport if the amount of intracellular labeled choline is greater in the non-agent-contacted host cell as compared to the agent-contacted host cell. Preferably, the difference in choline uptake between the tested first cell and the second cell is at least about a factor of two; more preferably, the difference is at least about a factor of five; most preferably, the difference is at least about an order of magnitude or greater.

Test agents, which include candidate binding partners, can be also be screened for the ability to bind to HACT polypeptides or polynucleotides or to affect HACT activity or HACT gene expression using high throughput screening. Using high throughput screening, many discrete agents can be tested in parallel so that large numbers of test agents can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. USA*. 19:1614-18 (1994). The cells are placed under agarose in petri dishes, then beads that carry combinatorial compounds are placed on the surface of the agarose. The combinatorial compounds are partially released from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadephia, Pa. (Nov. 7-10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2:57-63 (1996). In this example, combinatorial libraries were screened for compounds that had cytotoxic effects on cancer cells growing in agar.

For binding assays, the test agent is preferably a small molecule which binds to and inactivates the biological activity of the polypeptide. Examples of such small molecules include, but are not limited to, small peptides or peptide-like molecules. In binding assays, either the test agent or the HACT polypeptide can comprise a detectable label, such as a fluorescent, radioisotopic, chemiluminescent, or enzymatic label, such as horseradish peroxidase, alkaline phosphatase, or luciferase. Detection of a test agent which is bound to the HACT polypeptide can then be accomplished, for example, by direct counting of radioemmission, by scintillation counting, or by determining conversion of an appropriate substrate to a detectable product. Alternatively, binding of a test agent to an HACT polypeptide can be determined without labeling either of the interactants. For example, a microphysiometer can be used to detect binding of a test agent with an HACT polypeptide. A microphysiometer (e.g., Cytosensor®) is an analytical instrument that measures the rate at which a cell acidifies its environment using a light-addressable potentiometric sensor (LAPS). Changes in this acidification rate can be used as an indicator of the interaction between a test agent and an HACT polypeptide. (McConnell et al., *Science* 257:1906-1912, 1992).

Determining the ability of a test agent to bind to an HACT polypeptide also can be accomplished using a technology such as real-time Bimolecular Interaction Analysis (BIA) (Sjolander & Urbaniczky, *Anal. Chem.* 63:2338-2345, 1991, and Szabo et al., *Curr. Opin. Struct. Biol.* 5:699-705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an HACT polypeptide can be used as a "bait protein" in a two-hybrid assay or three-hybrid assay (see, e.g., U.S. Pat. No. 5,283,317; Zervos et al., *Cell,* 72:223-232, 1993; Madura et al., *J. Biol. Chem.* 268:12046-12054, 1993; Bartel et al., *Biotechniques,* 14:920-924, 1993; Iwabuchi et al., *Oncogene,* 8:1693-1696, 1993; and Brent WO94/10300) to identify other proteins which bind to or interact with the HACT polypeptide and modulate its activity.

The two-hybrid system is based on the modular nature of most transcription factors, which consist of separable DNA-binding and activation domains. Briefly, the assay utilizes two different DNA constructs. For example, in one construct a polynucleotide encoding an HACT polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the HACT polypeptide.

It may be desirable to immobilize either an HACT polypeptide (or polynucleotide) or the test agent to facilitate separation of bound from unbound forms of one or both of the interactants, as well as to accommodate automation of the assay. Thus, either the HACT polypeptide (or polynucleotide) or the test agent can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the HACT polypeptide (or polynucleotide) or test agent to a solid support, including use of covalent and non-covalent linkages, passive absorption, or pairs of binding moieties attached respectively to the polypeptide or test agent and the solid support. Test agents are preferably bound to the solid support in an array, so that the location of individual test agents can be tracked. Binding of a test agent to an HACT polypeptide (or polynucleotide) can be accomplished in any vessel suitable for containing the reactants. Examples of such vessels include microtiter plates, test tubes, and microcentrifuge tubes.

In one embodiment, an HACT polypeptide is a fusion protein comprising a domain that allows the HACT polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test agent and the non-adsorbed HACT polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either an HACT polypeptide (or polynucleotide) or a test agent can be immobilized utilizing conjugation of biotin and streptavidin. Biotinylated HACT polypeptides, polynucleotides, or test agents can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an HACT polypeptide, polynucleotides, or a test agent, but which do not interfere with a desired binding site, such as the active site of the HACT polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to an HACT polypeptide or test agent, enzyme-linked assays which rely on detecting an HACT activity of the HACT polypeptide, and SDS gel electrophoresis under non-reducing conditions.

Screening for test agents which bind to an HACT polypeptide or polynucleotide also can be carried out in an intact cell. Any cell which comprises an HACT polynucleotide or polypeptide can be used in a cell-based assay system. An HACT polynucleotide can be naturally occurring in the cell or can be introduced using techniques such as those described above. Either a primary culture or an established cell line can be used. An intact cell is contacted with a test agents. Binding of the test agent to an HACT polypeptide or polynucleotide is determined as described above, after lysing the cell to release the HACT polypeptide-or polynucleotide-test agent complex.

Test agents can be pharmacological agents already known in the art or can be compounds previously unknown to have any pharmacological activity. The agents can be naturally occurring or designed in the laboratory. They can be isolated from microorganisms, animals, or plants, and can be produced recombinantly, or synthesized by chemical methods known in the art. If desired, test agents can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12:145, 1997.

Methods for the synthesis of molecular libraries are well known in the art (see, for example, DeWitt et al., *Proc. Natl. Acad. Sci. U.S.A.* 90:6909, 1993; Erb et al. *Proc. Natl. Acad. Sci. U.S.A.* 91:11422, 1994; Zuckermann et al., *J. Med. Chem.* 37:2678, 1994; Cho et al., *Science,* 261:1303, 1993; Carell et al., *Angew. Chem. Int. Ed. Engl.* 33:2059, 1994; Carell et al., *Angew. Chem. Int. Ed. Engl.* 33:2061; Gallop et al., *J. Med. Chem.* 37:1233, 1994). Libraries of compounds can be presented in solution (see, e.g., Houghten, *Biotechniques* 13:412-421, 1992), or on beads (Lam, *Nature,* 354: 82-84, 1991), chips (Fodor, *Nature,* 364:555-556, 1993), bacteria or spores (Ladner, U.S. Pat. No. 5,223,409), plasmids (Cull et al., *Proc. Natl. Acad. Sci. U.S.A.* 89:1865-1869, 1992), or phage (Scott & Smith, *Science* 249:386-390, 1990; Devlin, *Science,* 249:404-406, 1990); Cwirla et al., *Proc. Natl. Acad. Sci.* 97:6378-6382, 1990; Felici, *J. Mol. Biol.* 222:301-310, 1991; and Ladner, U.S. Pat. No. 5,223, 409).

Compositions Comprising Polypeptides or Polynucleotides

The invention also provides pharmaceutical compositions which can be administered to a patient to achieve prevention, treatment, or amelioration of neurological and cognitive disorders such as pain, spasticity, myoclonus, muscle spasm, muscle hyperactivity, epilepsy, stroke, head trauma, neuronal cell death, multiple sclerosis, spinal cord injury, dystonia, Alzheimer's disease, Myasthenia Gravis, multi-infarct dementia, AIDS dementia, Parkinson's disease, Huntington's disease, amyotrophic lateral sclerosis (ALS), attention deficit disorder, nicotine addiction, organic brain syndromes, schizophrenia, and memory disorders. Pharmaceutical compositions of the invention can comprise, for example, a HACT polypeptide, HACT polynucleotide, antibodies which specifically bind to HACT polypeptide, or mimetics, agonists, antagonists, enhancers, or inhibitors of HACT activity. The compositions can be administered to a patient alone, or in combination with other agents or drugs.

Compositions of the invention can be delivered to a mammal, such as a rabbit, rat, mouse, guinea pig, chimpanzee, macaque, or human. Preferably the compositions are delivered to the central nervous system, and in particular the brain.

Compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, saline, buffered saline, dextrose, water, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, malodextrin, ethanol, or the like, singly or in combination, as well as substances such as wetting agents, emulsifying agents, or pH buffering agents. Liposomes can also be used as a carrier for a composition of the invention, see e.g., U.S. Pat. Nos. 5,786,214 and 6,096,716 for examples of delivery of polynucleotides and polypeptides to the central nervous system and brain. Eicosapetaenoic acid- or docosahexaenoic acid-conjugated polycationic carriers can also be used to deliver polynucleotides and polypeptides of the invention to the brain and central nervous system. See e.g., U.S. Pat. No. 5,716,614.

The compositions of the invention can be formulated into ingestable tablets, buccal tablets, troches, capsules, elixirs, suspensions, syrups, wafers, injectable formulations, suppositories, nasal sprays, nasal drops, and the like. The percentage of one or more polypeptides or polynucleotides of the invention in such compositions and preparations can vary from 0.1% to 60% of the weight of the unit.

The following are provided for exemplification purposes only and are not intended to limit the scope of the invention described in broad terms above. All references cited in this disclosure are incorporated herein by reference.

EXAMPLES

Example 1

Cloning of Human HACT cDNA

A pair of primers was designed on the basis of sequence alignment of rat high affinity choline transporter (GenBank accession number AB030947) and human genomic sequences, which were determined to have some homology to the rat HACT using the BLAST algorithm. The nucleotide primers were used to amplify the coding region of human high affinity choline transporter from a human brain cDNA library. The forward primer, HACT-F, had the sequence 5'-GCCATGGCTTCCCATGTGGAAGGAC-3' (SEQ ID NO: 5) and the reverse primer, HACT-R, had the sequence 5'-GGGTCATTGTAA(A/G)TTATCTTCA GTCCC-3' (SEQ ID NO:6). The primers were used under standard reaction conditions: initial denaturation at 94° C. for 2 min; 5 cycles of 94° C. for 30s, 55° C. for 30s, and 72° C. for 2 min; 30 cycles of 94° C. for 30s, 50° C. for 30s and 72° C. for 2 min; and final extension at 72° C. for 5 min. The PCR products were subjected to electrophoresis on a 1% agarose gel, and all resulting DNA fragments were excised, cloned, and sequenced. All obtained sequences were compared with rat HACT (GenBank accession number AB030947). One of the clones, designated number 14, was further characterized as a candidate for the high affinity choline transporter. Clone 14 was determined to comprise a human HACT polynucleotide as shown in SEQ ID NO: 1.

Example 2

Transporter Assay

A transporter assay for high affinity choline uptake was carried out using 293, HELA, and SF9 cells that had been transfected or infected with expression vectors (several eukaryotic expression vectors including pcDNA, AAV proviral vector, and Baculoviral vectors were used) either with or without a cDNA encoding human HACT. Briefly, $2 \times 10^5$ cells were incubated with tritiated choline chloride and various amounts of Hemicholinium-3 in 500 microliter media (20 mM HEPES, pH 7.4, 140 mM NaCl, 4 mM KCl, 1 mM $MgCl_2$, 1 mM $CaCl_2$) at 27° C. for 30 min in each transporter assay. The cells were then pelleted and washed three times before they were solublized in 1N NaOH and the tritium content determined by liquid scintillation counting. As shown in FIG. 1, cells expressing HACT has more than twice the activity compared with cells without HACT. Furthermore, the HACT activity was sensitive to 10 nM of Hemicholinium-3, which is characteristic of high affinity choline transporter. See e.g. Okuda et al. *Nat. Neurosci.* 3:120-5 (2000).

Figure 2:
FIG. 2 demonstrates SF9 cells infected with recombinant baculovirus expressing a human high affinity choline transporter-red fluorescent protein fusion protein. The human high affinity choline transporter-red fluorescent protein fusion protein is localized to the cell membrane.

A vector comprising a RFP (Red Fluorescent Protein) polynucleotide fused to the polynucleotide shown in SEQ ID NO: 1 was constructed using techniques well known in the art. Briefly, the stop codon of HACT was removed via PCR mediated mutagenesis and the HACT polynucleotide was inserted into an eukaryotic expression vector where RFP is fused at the C-terminus. The vector was transformed into a host cell and the host cell expressed a HACT-RFP fusion protein. The fusion protein was shown to be localized to the host cell membrane. Such a fusion was also generated in a recombinant baculovirus where the membrane association of HACT-RFP in SF9 cells can be ready observed. See FIG. 2.

Example 3

Expression of a Cytoplasmic Tail of HACT as an Antigen and Generation of a Monoclonal Antibody A C-terminal cytoplasmic tail (sCT, 83AAs from 498 to 580, numbered relative to SEQ ID NO:2) was PCR amplified and cloned into a modified histidine-tagged GFP fusion vector. The recombinant plasmid was introduced into bacterial strain JM105 and a recombinant fusion protein between a HACT C-terminal cytoplasmic domain and GFP was produced and affinity purified. The fusion protein was concentrated, dialyzed with PBS, and used as immunogen to immunize three mice for the purpose of development of a monoclonal antibody. The immunization was performed by the UF Hybridoma Core Laboratory.

Briefly, three 6-8 weeks old, female Balb/C mice, were injected with a 100 μL mixture of adjuvant and 25 μg antigen, which is a fusion of GFP with the cytoplasmic domain of HACT. Two more boosts were given in the $3^{rd}$ and $4^{th}$ week following the initial injection. A small amount of blood was taken from the tail vein of each mouse at day 10 after the last boost and the sera were assayed by ELISA and western blot. There was clearly an increased immunoglobulin titer specific to the cytoplasmic domain of HACT since both the original antigen and a different fusion protein comprising thioredoxin and the cytoplasmic domain of HACT were positive. Fusion was carried out with one mouse after a final boost of 25 μg of antigen was used intraperitoneally without adjuvant.

Protocols well know in the art were used in the development and screening of hybridoma specific to HACT. Briefly, spleen cells from one positive mouse were fused in the presence of PEG with a HL4 myeloma cell line and were plated out in five 96-well plates in the presence of HAT containing media. Ten days later, the supernatant was screened by ELISA using a soluble cytoplasmic domain containing antigen in a fusion with thioredoxin. The positive clones selected were transferred into 24 well plates and supplemented with HT containing media. One clone was selected and monoclonal antibodies were isolated and purified using techniques well known in the art. Briefly, 500 mL of supernatant from the culture of the positive hybridoma 5C10 was pooled from several batches and purified with a protein G column. The purified monoclonal antibody was used for western blot analysis for the expression of recombinant human HACT.

We claim:

1. A composition comprising an isolated high affinity choline transporter protein that has the amino acid sequence as shown in SEQ ID NO: 2, a polypeptide consisting of at least about six contiguous amino acids of the choline acetyltransferase polypeptide of SEQ ID NO: 4, and a pharmaceutically acceptable carrier.

2. A composition comprising an isolated polypeptide that consists of about at least 100 contiguous amino acids of a high affinity choline transporter as shown is SEQ ID NO: 2, a polypeptide consisting of at least about six contiguous amino acids of the choline acetyltransferase polypeptide of SEQ ID NO: 4, and a pharmaceutically acceptable carrier.

* * * * *